(12) United States Patent
Lee et al.

(10) Patent No.: US 12,246,069 B2
(45) Date of Patent: Mar. 11, 2025

(54) METHOD OF MAKING PRODRUG FOR SUSTAINED AND CONTROLLED RELEASE

(71) Applicant: University of Cincinnati, Cincinnati, OH (US)

(72) Inventors: Joo-Youp Lee, Cincinnati, OH (US); Edward Merino, Cincinnati, OH (US); Vishnu Sriram, Cincinnati, OH (US); Mina Jafari, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 52 days.

(21) Appl. No.: 17/442,949

(22) PCT Filed: Mar. 26, 2020

(86) PCT No.: PCT/US2020/024881
§ 371 (c)(1),
(2) Date: Sep. 24, 2021

(87) PCT Pub. No.: WO2020/198431
PCT Pub. Date: Oct. 1, 2020

(65) Prior Publication Data
US 2022/0184219 A1 Jun. 16, 2022

(51) Int. Cl.
*A61K 47/59* (2017.01)
*A61K 47/54* (2017.01)
*A61K 47/60* (2017.01)
*A61P 35/00* (2006.01)

(52) U.S. Cl.
CPC ............ *A61K 47/593* (2017.08); *A61K 47/54* (2017.08); *A61K 47/60* (2017.08); *A61P 35/00* (2018.01)

(58) Field of Classification Search
CPC ...... A61K 47/593; A61K 47/54; A61K 47/60; A61P 35/00
See application file for complete search history.

(56) References Cited

U.S. PATENT DOCUMENTS

| | | | | |
|---|---|---|---|---|
| 10,092,580 | B2 * | 10/2018 | Lichter | A61K 47/34 |
| 2016/0318849 | A1 * | 11/2016 | Merino | A61K 31/167 |
| 2017/0080092 | A1 * | 3/2017 | Cleland | A61K 47/593 |
| 2017/0340733 | A1 * | 11/2017 | Cao | A61K 31/502 |

OTHER PUBLICATIONS

Kruger et al.; Synthesis and Stability of Four Maleimide Derivatives of the Anticancer Drug Doxorubicin for the Preparation of Chemoimmunoconjugates; Pharmaceutical Society of Japan; Chem. Pharm. Bull. 45(2) 399-401 (1997) (Year: 1997).*
Shinohara et al.; Blackwell Publishing Asia Antitumor activity of sequence-specific alkylating agents: Pyrolle-imidazole CBI conjugates with indole linker; Japanese Cancer Association; Cancer Sci | Mar. 2006 | vol. 97 | No. 3 | 219-225 (Year: 2006).*
Yang et al.; The design, synthesis and in vitro immunosuppressive evaluation of novel isobenzofuran derivatives; Elsevier; Bioorganic & Medicinal Chemistry Letters 22 (2012) 53-56 (Year: 2012).*
Wong et al.; Mechanisms of Drug Release in Nanotherapeutic Delivery Systems; ACS Publications; Chem. Rev. 2015, 115, 3388-3432 (Year: 2015).*
Khandare et al; Polymer-drug conjugates: Progress in polymeric prodrugs; Elsevier; Prog. Polym. Sci. 31 (2006) 359-397 (Year: 2006).*
PLLA-PEG; https://specificpolymers.com/product/polyethylene-glycol-block-polylactic-acid/ (site accessed Apr. 2024) (Year: 2021).*
PDLLA-PEG; https://broadpharm.com/product/bp-29475 (site accessed Apr. 2024) (Year: 2024).*
PLGA-PEG; https://creativepegworks.com/structure/peg-plga-copolymer (site accessed Apr. 2024) (Year: 2022).*
Poly AA; https://www.sigmaaldrich.com/US/en/technical-documents/technical-article/materials-science-and-engineering/drug-delivery/poly-amino-acid-block-copolymers (Year: 2021).*
International Search Report mailed Aug. 26, 2020 in reference to co-pending PCT/US2020/024881 filed Mar. 26, 2020. 9 pgs.
Yang et al. "The design, synthesis and in vitro immunosuppressive evaluation of novel isobenzofuran derivatives", Bioorganic and Medicinal Chemistry Letters. 2012. vol. 22, pp. 53-56, entire document, especially: p. 53, col. 2, para 2; p. 55, col. 2, para 3; p. 55, Table 3, Compd Sf.
Shinohara et al. "Antitumor activity of sequence-specific alkylating agents: Pyrolle-imidazole CBI conjugates with indole linker", Cancer Sci. 2006. vol. 97(3), pp. 219-225, entire document, especially: abstract; Figure 2a, formula 1.
Hocherl et al. "One-pot synthesis of reactive oxygen species (ROS)-self-immolative polyoxalate prodrug nanoparticles for hormone dependent cancer therapy with minimized side effects", Polym. Chem. 2017. vol. 8, pp. 1999-2004, entire document.
Kapuriya et al. "Novel DNA-directed alkylating agents: Design, synthesis and potent antitumor effect of phenyl N-mustard-9-anilinoacridine conjugates via a carbamate or carbonate linker", Bioorganic & Medicinal Chemistry. 2009. vol. 17, pp. 1264-1275, entire document.
X. Xu, P.E. Saw, W. Tao, Y. Li, X. Ji, S. Bhasin, Y. Liu, D. Ayyash, J. Rasmussen, M. Huo, ROS-13 Responsive Polyprodrug Nanoparticles for Triggered Drug Delivery and Effective Cancer Therapy, Advanced Materials, 29 (2017).
J. Shi, P.W. Kantoff, R. Wooster, O.C. Farokhzad, Cancer nanomedicine: progress, challenges and opportunities, Nat Rev Cancer, 17 (2017) 20-37.

(Continued)

*Primary Examiner* — Robert A Wax
*Assistant Examiner* — John W Lippert, III
(74) *Attorney, Agent, or Firm* — Brent M. Peebles (57) ABSTRACT

A novel ROS-responsive prodrug is provided. The prodrug utilizes a unique modified oxalate linker conjugated to 4-aminophenol, which can enhance the reaction kinetics for intracellular ROS within tumor tissues while keeping the modified oxalate backbone stable with amide bond under very low ROS level.

22 Claims, 5 Drawing Sheets

(56) References Cited

OTHER PUBLICATIONS

H. Yoo, J. Oh, K. Lee, T. Park, Biodegradable Nanoparticles Containing Doxorubicin-PLGA Conjugate for Sustained Release, Pharm Res, 16 (1999) 1114-1118.
A. Ponta, Y. Bae, Tumor-preferential sustained drug release enhances antitumor activity of block copolymer micelles, Journal of drug targeting, 22 (2014) 619-628.
J. Panyam, V. Labhasetwar, Biodegradable nanoparticles for drug and gene delivery to cells and tissue, Advanced Drug Delivery Reviews, 64, Supplement (2012) 61-71.
J. Shi, Y. Xu, X. Xu, X. Zhu, E. Pridgen, J. Wu, A.R. Votruba, A. Swami, B.R. Zetter, O.C. Farokhzad, Hybrid lipid-polymer nanoparticles for sustained siRNA delivery and gene silencing, Nanomedicine: Nanotechnology, Biology and Medicine, 10 (2014) 897-900.
N. Kamaly, B. Yameen, J. Wu, O.C. Farokhzad, Degradable controlled-release polymers and polymeric nanoparticles: mechanisms of controlling drug release, Chemical reviews, 116 (2016) 2602-2663.
M. Elsabahy, K.L. Wooley, Design of polymeric nanoparticles for biomedical delivery applications, Chemical Society Reviews, 41 (2012) 2545-2561.
G. Chen, I. Roy, C. Yang, P.N. Prasad, Nanochemistry and nanomedicine for nanoparticle-based diagnostics and therapy, Chemical reviews, 116 (2016) 2826-2885.
P. Bawa, V. Pillay, Y.E. Choonara, L.C. Du Toit, Stimuli-responsive polymers and their applications in drug delivery, Biomedical materials, 4 (2009) 022001.
E.-J. Cha, I.-C. Sun, S.C. Lee, K. Kim, I.C. Kwon, C.-H. Ahn, Development of a pH sensitive nanocarrier using calcium phosphate coated gold nanoparticles as a platform for a potential theranostic material, Macromolecular research, 20 (2012) 319-326.
Z. Zhou, A. Badkas, M. Stevenson, J.Y. Lee, Y.K. Leung, Herceptin conjugated PLGA-PHis-PEG pH sensitive nanoparticles for targeted and controlled drug delivery, Int J Pharm, 487 (2015) 81-90.
J.S. Katz, J.A. Burdick, Light-Responsive Biomaterials: Development and Applications, Macromolecular bioscience, 10 (2010) 339-348.
S. Medeiros, A. Santos, H. Fessi, A. Elaissari, Stimuli-responsive magnetic particles for biomedical applications, International journal of pharmaceutics, 403 (2011) 139-161.
R.A. Mitteer, Y. Wang, J. Shah, S. Gordon, M. Fager, P.-P. Butter, H.J. Kim, C. Guardiola-Salmeron, A. Carabe-Fernandez, Y. Fan, Proton beam radiation induces DNA damage and cell apoptosis in glioma stem cells through reactive oxygen species, Scientific reports, 5 (2015).
M. Sertorio, J.P. Perentesis, R.E. Vatner, A.E. Mascia, Y. Zheng, S.I. Wells, Cancer Cell Metabolism: Implications for X-ray and Particle Radiation Therapy, International Journal of Particle Therapy, 5 (2018) 40-48.
D. Trachootham, J. Alexandre, P. Huang, Targeting cancer cells by ROS-mediated mechanisms: a radical therapeutic approach?, Nature reviews Drug discovery, 8 (2009) 579-591.
B.C. Dickinson, C.J. Chang, Chemistry and biology of reactive oxygen species in signaling or stress responses, Nat Chem Biol, 7 (2011) 504.
M.P. Murphy, How mitochondria produce reactive oxygen species, Biochem J, 417 (2009) 1-13.
J. Takahashi, M. Misawa, Characterization of reactive oxygen species generated by protoporphyrin IX under X-ray irradiation, Radiation Physics and Chemistry, 78 (2009) 889-898.
S.-J. Seo, J.-K. Jeon, S.-M. Han, J.-K. Kim, Reactive oxygen species-based measurement of the dependence of the Coulomb nanoradiator effect on proton energy and atomic Z value, International journal of radiation biology, 93 (2017) 1239-1247.
P. Riley, Free radicals in biology: oxidative stress and the effects of ionizing radiation, International journal of radiation biology, 65 (1994) 27-33.
D. Schulz-Ertner, H. Tsujii, Particle radiation therapy using proton and heavier ion beams, Journal of clinical oncology, 25 (2007) 953-964.
J.P.C. Grutters, A.G.H. Kessels, M. Pijls-Johannesma, D. De Ruysscher, M.A. Joore, P. Lambin, Comparison of the effectiveness of radiotherapy with photons, protons and carbon-ions for non-small cell lung cancer: A meta-analysis, Radiotherapy and Oncology, 95 (2010) 32-40.
M.S. Shim, Y. Xia, A reactive oxygen species (ROS)—responsive polymer for safe, efficient, and targeted gene delivery in cancer cells, Angewandte Chemie International Edition, 52 (2013) 6926-6929.
Z. Zhou, M. Jafari, V. Sriram, J. Kim, J.Y. Lee, S.J. Ruiz-Torres, S.E. Waltz, Delayed Sequential Co-Delivery of Gefitinib and Doxorubicin for Targeted Combination Chemotherapy, Mol Pharm, 14 (2017) 4551-4559.

* cited by examiner

METHOD OF MAKING PRODRUG FOR SUSTAINED AND CONTROLLED RELEASE

CROSS REFERENCE TO RELATED APPLICATIONS

The present application is a continuation of PCT Application No. PCT/US2020/024881, filed on Mar. 26, 2020, which claims the benefit of U.S. Provisional Application Ser. No. 62/823,740, filed Mar. 26, 2019, which application is hereby incorporated by reference in its entirety.

TECHNICAL FIELD

The present invention relates to a method and composition for treating cancer. More specifically, this invention relates to a prodrug that targets cancer cells with an elevated ROS level.

BACKGROUND OF THE INVENTION

The ideal goals for cancer treatment are to maximize antitumor therapeutic efficacy and minimize side effects. Nanoparticles have made tremendous progress in advancing these goals. Most therapeutic nanoparticles for solid tumor treatment are administered systemically. One of the major limiting hurdles of nanoparticle-mediated cancer therapeutics is premature drug leakage that leads to poor antitumor efficacy and off-target activity. Therefore, challenges arise when balancing sustained release during systemic circulation and controlled release at the tumor site. A polymer-prodrug conjugate approach can address these challenges by deactivating drugs upon conjugation to a polymer and reactivating them upon a release that is triggered by a stimulus-response mechanism. The controlled release may be achievable by either internal or external stimuli such as pH levels, enzyme presence, reactive oxygen species (ROS) levels, magnetic field, light, ultrasound, and irradiation. Among these potential mechanisms, ROS levels can serve as both internal and external stimuli. The ROS level in cancerous cells can be up to 5,000 times higher than those in blood and healthy cells, and can go even higher upon irradiation commonly used in many cancer treatments. However, most ROS approaches to chemotherapy problematically respond to low ROS levels. Therefore, a need exists for a nanoparticle based therapeutic that responds to higher levels of ROS found in microenvironments within the body.

SUMMARY OF THE INVENTION

The present invention addresses this need with a novel ROS-responsive prodrug design that utilizes a unique modified oxalate linker conjugated to 4-aminophenol, which can enhance the reaction kinetics for intracellular ROS within tumor tissues while keeping the modified oxalate backbone stable with amide bond under very low ROS level.

In one embodiment of the present invention, a compound of formula (1) is disclosed:

(1)

or a pharmaceutically acceptable salt or solvate thereof, wherein, independently for each occurrence:
X is NH or O;
Y is O, S, or $NR^2$;
Z is OH, $OR^2$, $NHR^2$, or $SR^2$;
$R^1$ is a chemotherapeutic agent selected from the group consisting of alkylating agents; purine and pyrimidine analogs and derivatives; topoisomerase inhibitors; taxanes; antifolates; angiogenesis inhibitors; anti-tumor monoclonal antibodies; cytotoxic antibiotics; anthracycline antibiotics; triterpenoid Stat3 inhibitors; and physiologically acceptable salts thereof; and
$R^2$ is a polymer selected from the group consisting of PLLA-PEG, PDLLA-PEG, PLGA-PEG, Poly (L-aspartic acid), Poly (L-lysine), Poly (L-glutamic acid), Poly (L-arginine), and Poly (L-ornithine); or $R^2$ is a linkage to said polymer.

In one embodiment, the compound is encapsulated in a nanoparticle. In another embodiment, the compound is physically encapsulated in a nanoparticle. In one embodiment, the compound is hydrophobic and the nanoparticle comprises a polymer selected from the group consisting of PLLA-PEG, PDLLA-PEG and PLGA-PEG. In another embodiment, the compound is hydrophilic and the nanoparticle comprises a polymer selected from the group consisting of albumin, Poly (L-aspartic acid), Poly (L-lysine), Poly (L-glutamic acid), Poly (L-arginine), and Poly (L-ornithine).

In one embodiment, $R^1$ is an anthracycline antibiotic selected from the group consisting of doxorubicin, epirubicin, daunorubicin, valrubicin and idarubicin. In another embodiment, $R^1$ is doxorubicin.

In another embodiment, $R^1$ is an alkylating agent selected from the group consisting of cisplatin, carboplatin, oxaliplatin, mechlorethamine, cyclophosphamide, chlorambucil and ifosfamide. In one embodiment, $R^1$ is cisplatin.

In one embodiment, X is NH. In one embodiment, Y is O. In another embodiment, Z is $OR^2$.

In another embodiment of the present invention, a method for treatment of cancer in a subject in need thereof is disclosed. The method involves administering to the subject a therapeutically effective amount of a compound having compound of formula (1):

(1)

or a pharmaceutically acceptable salt or solvate thereof, wherein, independently for each occurrence:
X is NH or O;
Y is O, S, or $NR^2$;
Z is OH, $OR^2$, $NHR^2$, or $SR^2$;
$R^1$ is a chemotherapeutic agent selected from the group consisting of alkylating agents; purine and pyrimidine analogs and derivatives; topoisomerase inhibitors; taxanes; antifolates; angiogenesis inhibitors; anti-tumor monoclonal antibodies; cytotoxic antibiotics; anthracycline antibiotics; triterpenoid Stat3 inhibitors; and physiologically acceptable salts thereof; and
$R^2$ is a polymer selected from the group consisting of PLLA-PEG, PDLLA-PEG, PLGA-PEG, Poly (L-aspartic acid), Poly (L-lysine), Poly (L-glutamic acid), Poly (L-arginine), and Poly (L-ornithine); or $R^2$ is a linkage to said polymer.

In one embodiment, the compound is encapsulated in a nanoparticle by means of chemical conjugation. In another embodiment, the compound is physically encapsulated in a nanoparticle. In one embodiment, the compound is hydrophobic and the nanoparticle comprises a polymer selected from the group consisting of PLLA-PEG, PDLLA-PEG and PLGA-PEG. In another embodiment, the compound is hydrophilic and the nanoparticle comprises a polymer selected from the group consisting of albumin, Poly (L-aspartic acid), Poly (L-lysine), Poly (L-glutamic acid), Poly (L-arginine), and Poly (L-ornithine).

In one embodiment, $R^1$ is an anthracycline antibiotic selected from the group consisting of doxorubicin, epirubicin, daunorubicin, valrubicin and idarubicin. In another embodiment, $R^1$ is doxorubicin.

In another embodiment, $R^1$ is an alkylating agent selected from the group consisting of cisplatin, carboplatin, oxaliplatin, mechlorethamine, cyclophosphamide, chlorambucil and ifosfamide. In one embodiment, $R^1$ is cisplatin.

In one embodiment, $R^2$ is a polymer selected from the group consisting of PLLA-PEG, PDLLA-PEG and PLGA-PEG. In another embodiment, X is NH. In one embodiment, Y is O. In another embodiment, Z is $OR^2$.

In an embodiment of the present invention, the method further comprises administering radiation to the subject in conjunction with the compound. In one embodiment, the radiation is proton radiation.

BRIEF DESCRIPTION OF THE DRAWINGS

The foregoing summary, as well as the following detailed description of preferred embodiments of the application, will be better understood when read in conjunction with the appended drawings.

DETAILED DESCRIPTION OF THE INVENTION

The details of one or more embodiments of the disclosed subject matter are set forth in this document. Modifications to embodiments described in this document, and other embodiments, will be evident to those of ordinary skill in the art after a study of the information provided herein.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The term "target", as used herein, refers to the cell type or tissue to which enhanced delivery of the therapeutic agent is desired. For example, diseased tissue may be a target for therapy.

An "effective amount" or "therapeutically effective amount" of a composition, as used herein, is a predetermined amount calculated to achieve a desired effect.

As used herein, the term "therapeutic agent" means a compound utilized to image, impact, treat, combat, ameliorate, prevent or improve an unwanted condition or disease of a patient. In an embodiment, disclosed long-circulating nanoparticles include a therapeutic agent and biodegradable and/or biocompatible polymeric particles, optionally functionalized with targeting moieties. The nanoparticles are designed to circulate in a vascular compartment of a patient for an extended period of time, distribute and accumulate at a target, and release the encapsulated therapeutic agent in a controlled manner. These characteristics can result in an increased level of therapeutic agent in the target and a potential reduction in off-target exposure. For example, the disclosed nanoparticles remain in circulation longer because, upon administration to a patient (e.g. a mammal, primate (e.g. human)), the disclosed nanoparticles are substantially confined to the vascular compartment of the patient, and are engineered to be cleared very slowly.

While the following terms are believed to be well understood by one of ordinary skill in the art, definitions are set forth to facilitate explanation of the disclosed subject matter. Unless defined otherwise, all technical and scientific terms used herein have the same meaning as commonly understood by one of ordinary skill in the art to which the disclosed subject matter belongs.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

One of the major limiting hurdles of nanoparticle ("NP")-mediated cancer therapeutics is reported to be premature drug leakage. Most therapeutic NPs for solid tumor treatment are administered systemically. Maximum anti-tumor therapeutic efficacy and minimum side effects are ideal treatment goals for cancer treatment. Although NP-based therapeutics made tremendous progress, it is still a great challenge to meet the goals due to the two desired but conflicting concepts of sustained release during systemic circulation and controlled release at the tumor site. Many NP-based therapeutics have not become commercialized due to premature drug leakage, leading to poor anti-tumor efficacy and off-target activity. A polymer-prodrug conjugate approach can address the above two great challenges by deactivating potent but toxic drugs upon conjugation to polymer and reactivating them upon release triggered by a stimulus-response mechanism. At the tumor site, the controlled release of prodrug is achievable by the presence of reactive oxygen species (ROS). The ROS level in cancerous cells can be up to ~5,000 times higher than those in blood and healthy cells. It can go even higher upon irradiation commonly used in many cancer treatments. Ionizing radiation can generate hydroxyl (OH·) radicals that effectively trigger controlled drug release. Breast cancers (BCs) are reported to show persistently high metabolic ROS level compared with normal cells related to mitochondrial dysfunction. Estrogens and metabolites of estrogen also produce ROS in BC cells.

Figure 2A:
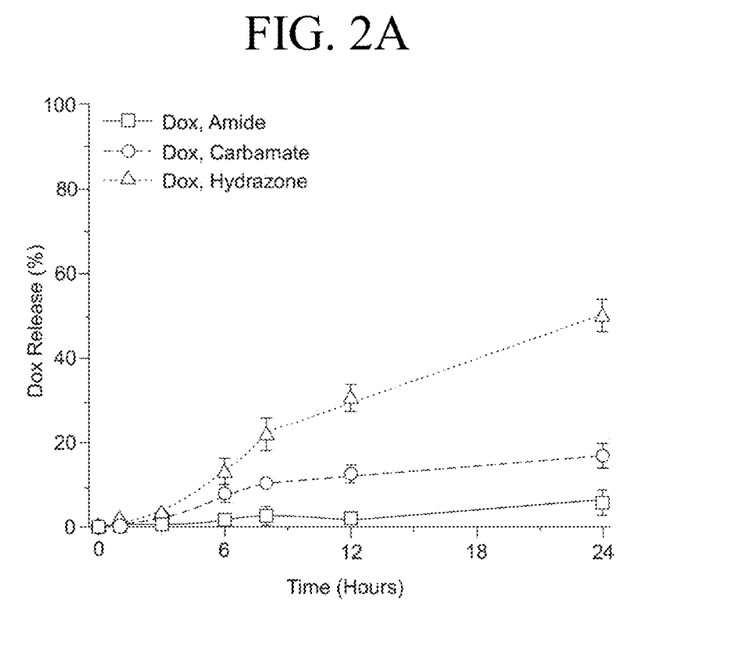
FIG. 2A is a graph showing the release kinetics of Dox conjugates to a polymer via amide, carbamate, and hydrazone bonds at pH 7.0.
Figure 2B:
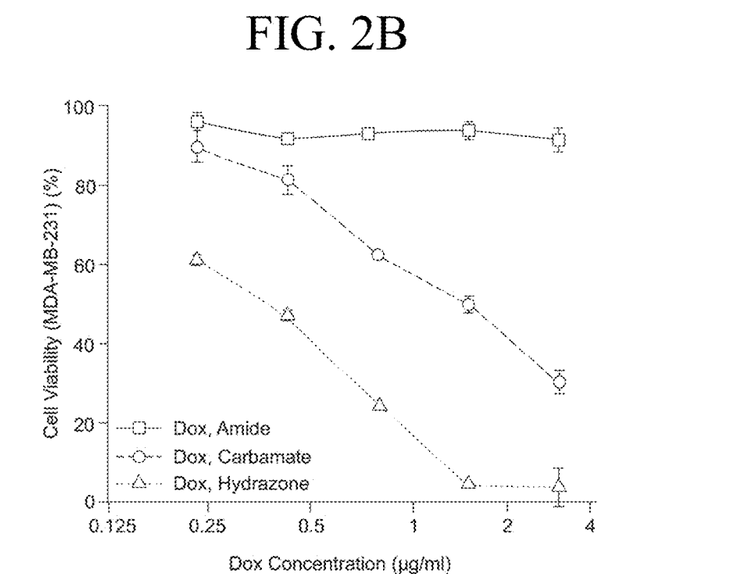
FIG. 2B is a graph showing the cytotoxicity against MDA-MB-231 cell line for Dox conjugates to a polymer via amide, carbamate, and hydrazone bonds.

A commonly used chemotherapeutic, doxorubicin ("Dox") is widely used for BC treatment. However, cardiotoxicity is a major side effect. As part of the present invention, we tested the impacts of Dox molecules conjugated through the primary amine group on Dox to a polymer using different chemical bonds on release and cytotoxicity (FIGS. 2A and 2B). We found that the different cytotoxicity resulting from different Dox release kinetics derived from the different bonds. Among the amide, carbamate, and hydrazone bonds, the amide bond showed the slowest Dox release kinetics and thus the minimal cytotoxicity. We have surprisingly discovered that using the very stable amide bond around an ROS-responsive linker conjugated to a chemotherapeutic drug such as a Dox molecule and a polymer produces a novel prodrug-polymer conjugate.

Our ROS-responsive prodrug (shown in Formula 1) utilizes a very unique modified oxalate linker conjugated to 4-aminophenol, which can enhance the reaction kinetics for intracellular ROS within tumor tissues while keeping the modified oxalate backbone stable with amide bond under very low ROS level (FIGS. 2A and 2B).

(Formula 1)

Formula 1 shows an embodiment of the ROS-responsive prodrug of the present invention. Alternative embodiments include pharmaceutically acceptable salts or solvates thereof. For Formula 1, independently for each occurrence:

X is NH or O;
Y is O, S, or $NR^2$;
Z is OH, $OR^2$, $NHR^2$, or $SR^2$;
$R^1$ is a chemotherapeutic agent selected from the group consisting of alkylating agents; purine and pyrimidine analogs and derivatives; topoisomerase inhibitors; taxanes; antifolates; angiogenesis inhibitors; anti-tumor monoclonal antibodies; cytotoxic antibiotics; anthracycline antibiotics; triterpenoid Stat3 inhibitors; and physiologically acceptable salts thereof; and
$R^2$ is a polymer selected from the group consisting of PLLA-PEG, PDLLA-PEG, PLGA-PEG, Poly (L-aspartic acid), Poly (L-lysine), Poly (L-glutamic acid), Poly (L-arginine), and Poly (L-ornithine); or $R^2$ is a linkage to said polymer. In one embodiment, $R^2$ is a polymer selected from the group consisting of Poly (L-aspartic acid), Poly (L-lysine), Poly (L-glutamic acid), Poly (L-arginine), and Poly (L-ornithine).

In one embodiment, the compound is encapsulated in a nanoparticle. In another embodiment, the nanoparticle comprises a polymer selected from the group consisting of PLLA-PEG, PDLLA-PEG, PLGA-PEG, Poly (L-aspartic acid), Poly (L-lysine), Poly (L-glutamic acid), Poly (L-arginine), and Poly (L-ornithine).

In another embodiment, the compound is physically encapsulated in a nanoparticle. In one embodiment, the compound is hydrophobic and the nanoparticle comprises a polymer selected from the group consisting of PLLA-PEG, PDLLA-PEG and PLGA-PEG. In another embodiment, the compound is hydrophilic and the nanoparticle comprises a polymer selected from the group consisting of albumin, Poly (L-aspartic acid), Poly (L-lysine), Poly (L-glutamic acid), Poly (L-arginine), and Poly (L-ornithine).

This design approach can significantly reduce the cytotoxicity of chemotherapeutic drugs (such as Dox) even under the premature drug leakage of the prodrug, and effectively release the chemotherapeutic accumulated at tumor sites by innate intracellular ROS and potentially by extra intracellular ROS induced by irradiation.

Linker

Peroxalate derivatives are a class of reactive oxygen species (ROS)-responsive compounds. Peroxalate esters, a well-known group of this family with very high reactivity towards $H_2O_2$, hold a great promise as an ROS-responsive prodrug approach. But, conventional peroxalate esters are not quite stable in aqueous media and prone to hydrolysis, which can limit their application. On the other hand, their aliphatic amide derivative, peroxamides, are more stable during hydrolysis but poorly reactive toward oxidation. The compound of the present invention includes an aromatic ring to one side of the peroxamide. Therefore, we produced a novel oxalate linker with high stability and reactivity.

Polymer Conjugate

In some embodiments, the prodrug of the present invention is conjugated to a polymer. In some embodiments, the polymer may be PLLA-PEG, PDLLA-PEG, PLGA-PEG, Poly (L-aspartic acid), Poly (L-lysine) (PLy hereafter), Poly (L-glutamic acid), Poly (L-arginine), or Poly (L-ornithine). In one embodiment, the conjugate is Dox-PLy. We have found that the Dox-PLy conjugate has a very stable amide bond that shows very slow Dox release (i.e. <~10% after 96 hrs) under normal physiological conditions at pH 7.0, and thus has insignificant cytotoxicity (data not shown).

Chemotherapeutic Agent

The compositions described herein can beneficially incorporate a wide variety of anti-cancer chemotherapeutic agents (e.g., an anti-tumor agent) for targeted delivery to tumors. Non-limiting examples of such chemotherapeutic agents include: alkylating agents (e.g., cisplatin; carboplatin; oxaliplatin; mechlorethamine; cyclophosphamide; chlorambucil; ifosfamide); purine and pyrimidine analogs and derivatives (e.g., 5-fluorouricil; floxuridine; cytosine arabinoside; mercaptopurine; thioguanine; azathioprine; fludarabine; pentostatin; cladribine); topoisomerase inhibitors (e.g., etoposide; etoposide phosphate; teniposide; amsacrine); taxanes (e.g., paclitaxel); antifolates (e.g., methotrexate; trimethoprim, pyrimethamine; pemetrexed); angiogenesis inhibitors (e.g., vitaxin; anecorvate, angiostatin; endostatin; squalamine; antiangiogenic tryptophanyl-t-RNA sythetase fragments, such as T2-TrpRS); anti-tumor monoclonal antibodies (e.g., bevacizumab; tivozanib; vandetanib; vatalanib; alemtuzumab; cetuximab; gemtuzumab; ibritumomab; pantitumumab; rituximab; tositumomab; trastuzumab); and other anti-neoplastic or chemotherapeutic agents, such as cytotoxic antibiotics (e.g., actinomycin; bleomycin; plicamycin; mitomycin); anthracycline antibiotics (e.g., doxorubicin; epirubicin; daunorubicin; valrubicin; idarubicin); triterpenoid Stat3 inhibitors (e.g., ursolic acid; a 2-cyano-3,12-dioxooleana-1,9-dien-28-oic ester; a 2-cyano-3,12-dioxooleana-1,9-dien-28-oic amide such as 1-[2-cyano-3-,12-dioxooleana-1,9(11)-dien-28-oyl]imidazole (also known as CDDO-Im)); and the like, as well as physiologically acceptable salts thereof. In one embodiment, the chemotherapeutic agent is Dox. In another embodiment, the chemotherapeutic agent is cisplatin.

Radiation

The ROS-responsive prodrug of the present invention can suppress the release of the chemotherapeutic agent during systemic circulation and control its release by responding to intracellular ROS at the tumor sites. The ROS level in cancerous cells can be up to ~5,000 times higher than those in blood and healthy cells. These levels can go even higher upon X-ray or proton radiation that is commonly used in many cancer treatments. Ionizing radiation can generate hydroxyl (OH) radicals that effectively trigger controlled drug release. In one embodiment, x-ray radiation is used. In some embodiments, photon or proton radiation is used.

In one embodiment, proton therapy is used to give a very localized treatment with higher local OH radical generation. Proton radiation could reduce damage to healthy tissues. Levels and amounts of radiation will vary according to the overall therapy plan for the patient. An example of such a radiation therapy plan for a breast cancer patient is a total 50 Gy (=2 Gy/day×25 days) followed by a boost of 10 Gy, also in 2 Gy fractions to the tumor bed. Alternatively, hypofractionation may be used, involving a higher dosage for a shorter period of time. In another embodiment, the number of radiation fractions is lower, for example 15 or 16, with 2.5 Gy or 2.56 Gy per day.

Nanoparticle

In general, a "nanoparticle" refers to any particle having a diameter of less than 1,000 nm, e.g. about 10 nm to about 200 nm. Disclosed therapeutic nanoparticles may include nanoparticles having a diameter of about 20 to about 140 nm, or about 40 to about 130 nm, or about 60 to about 120 nm.

Disclosed nanoparticles may include about 0.2 to about 35 weight percent, about 3 to about 40 weight percent, about 5 to about 30 weight percent, 10 to about 30 weight percent, 15 to 25 weight percent, or even about 4 to about 25 weight percent of a chemotherapeutic agent, such as Dox.

In some embodiments, the nanoparticles disclosed herein include one, two, three or more biocompatible and/or biodegradable polymers. For example, a contemplated nanoparticle may include about 10 to about 99 weight percent of a one or more block co-polymers that include a biodegradable polymer and polyethylene glycol, and about 0 to about 50 weight percent of a biodegradable homopolymer.

Any polymer can be used in accordance with the present invention. Polymers can be natural or unnatural (synthetic) polymers. Polymers can be homopolymers or copolymers comprising two or more monomers. In terms of sequence, copolymers can be random, block, or comprise a combination of random and block sequences. In some embodiments, the polymer of the nanoparticle is PLLA-PEG, PDLLA-PEG, PLGA-PEG, Poly (L-aspartic acid), Poly (L-lysine), Poly (L-glutamic acid), Poly (L-arginine), or Poly (L-ornithine).

The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, i.e., a biopolymer. Non-limiting examples include peptides or proteins. In some cases, additional moieties may also be present in the polymer, for example biological moieties such as those described below. If more than one type of repeat unit is present within the polymer, then the polymer is said to be a "copolymer". It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid ("PLLA"), poly-D-lactic acid ("PDLA"), poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly(4-hydroxy-L-proline ester), poly [α-(4-aminobutyl)-L-glycolic acid], and derivatives thereof.

Disclosed nanoparticles may have a substantially spherical (i.e., the particles generally appear to be spherical), or non-spherical configuration. For instance, the particles, upon swelling or shrinkage, may adopt a non-spherical configuration.

Disclosed nanoparticles may have a characteristic dimension of less than about 1 micrometer, where the characteristic dimension of a particle is the diameter of a perfect sphere having the same volume as the particle.

Disclosed nanoparticles may be stable (e.g. retain substantially all active agent) for example in a solution that may contain a saccharide, for at least about 3 days, about 4 days or at least about 5 days at room temperature, or at 25° C.

In another embodiment, the particles may be albumin, such as human serum albumin, or nanostructured lipid carriers (NLCs). NLCs are a class of lipid nanoparticles with a solid lipid matrix at room temperature. They consist of a mixture of a solid lipid and oil, with a ratio of 70:30 and up to a ratio of 99.9:0.1. The NLCs are made of biodegradable and biocompatible lipids and surfactants/stabilizers. Choice of the solid lipids includes Cetylpalmitate, Compritol 888 ATO, Glycerol monostearate, Palmitic acid, Stearic acid, and Tristearin. Liquid lipids (oils) can be chosen among Castor oil, Oleic acid, and Miglyol 812. Soybean lecithin, Sorbitan trioleate, Soybean phosphatidylcholine, Poloxamer 188, and Polyvinyl alcohol are good options as a surfactant Preparation of Nanoparticles Another aspect of this disclosure is directed to systems and methods of making nanoparticles incorporating the prodrug of the present invention. In some embodiments, using two or more different polymers (e.g., copolymers, e.g., block copolymers) in different ratios and producing particles from the polymers (e.g., copolymers, e.g., block copolymers), properties of the particles be controlled.

In one set of embodiments, the nanoparticles are formed by providing a solution comprising one or more polymers, and contacting the solution with a polymer nonsolvent to produce the particle. The solution may be miscible or immiscible with the polymer nonsolvent. For example, a water-miscible liquid such as acetonitrile may contain the polymers, and particles are formed as the acetonitrile is contacted with water, a polymer nonsolvent, e.g., by pouring the acetonitrile into the water at a controlled rate. The polymer contained within the solution, upon contact with the polymer nonsolvent, may then precipitate to form particles such as nanoparticles. Two liquids are said to be "immiscible" or not miscible, with each other when one is not soluble in the other to a level of at least 10% by weight at ambient temperature and pressure. Typically, an organic solution (e.g., dichloromethane, acetonitrile, chloroform, tetrahydrofuran, acetone, formamide, dimethylformamide, pyridines, dioxane, dimethysulfoxide, etc.) and an aqueous liquid (e.g., water, or water containing dissolved salts or other species, cell or biological media, ethanol, etc.) are immiscible with respect to each other. For example, the first solution may be poured into the second solution (at a suitable rate or speed). In some cases, particles such as nanoparticles may be formed as the first solution contacts the immiscible second liquid, e.g., precipitation of the polymer upon contact causes the polymer to form nanoparticles while the first solution poured into the second liquid, and in some cases, for example, when the rate of introduction is carefully controlled and kept at a relatively slow rate, nanoparticles may form. The control of such particle formation can be readily optimized by one of ordinary skill in the art using only routine experimentation.

Pharmaceutical Formulations

Nanoparticles disclosed herein may be combined with pharmaceutical acceptable carriers to form a pharmaceutical composition, according to another aspect of the invention. As would be appreciated by one of skill in this art, the carriers may be chosen based on the route of administration as described below, the location of the target issue, the drug being delivered, the time course of delivery of the drug, etc.

The pharmaceutical compositions of this invention can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles of the present invention are administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

It will be appreciated that the exact dosage of the prodrug of the present invention is chosen by the individual physician in view of the patient to be treated, in general, dosage and administration are adjusted to provide an effective amount of the prodrug to the patient being treated. As used herein, the "effective amount" of the prodrug refers to the amount necessary to elicit the desired biological response. As will be appreciated by those of ordinary skill in this art, the effective amount of the prodrug may vary depending on such factors as the desired biological endpoint, the drug to be delivered, the target tissue, the route of administration, etc. For example, the effective amount of the prodrug containing an anti-cancer drug might be the amount that results in a reduction in tumor size by a desired amount over a desired period of time. Additional factors which may be taken into account include the severity of the disease state; age, weight and gender of the patient being treated; diet; time and frequency of administration; drug combinations; reaction sensitivities; and tolerance/response to therapy.

Methods of Treatment

In some embodiments, the prodrug of the present invention may be used to treat, alleviate, ameliorate, relieve, delay onset of, inhibit progression of, reduce severity of, and/or reduce incidence of one or more symptoms or features of a disease, disorder, and/or condition. The present invention is a drug releasing platform that liberates a drug molecule over time. While we have discussed ROS in the context of cancer cells, there are several other indications that are caused by overactive ROS in the body. These include conditions such as allergy, asthma, inflammatory bowel disease (IBD), eczema, and psoriasis. In each of these, the initiator of the ROS is the immune system, and this technology can be used to deliver anti-histamines, corticosteroids, or pain medication.

In some embodiments, the prodrug of the present invention may be used to treat solid tumors, e.g., cancer and/or cancer cells. In certain embodiments, the prodrug may be used to treat any cancer wherein with elevated ROS on the surface of cancer cells or in the tumor. Examples of such conditions include, but are not limited to, breast cancer, bladder cancer, lymphoma, leukemia, lung, head and neck cancer, brain cancer, cervical and ovarian cancer.

The term "cancer" includes pre-malignant as well as malignant cancers. Cancers include, but are not limited to, prostate, gastric cancer, colorectal cancer, skin cancer, e.g., melanomas or basal cell carcinomas, lung cancer, breast cancer, cancers of the head and neck, bronchus cancer, pancreatic cancer, urinary bladder cancer, brain or central nervous system cancer, peripheral nervous system cancer, esophageal cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. "Cancer cells" can be in the form of a tumor, exist alone within a subject (e.g., leukemia cells), or be cell lines derived from a cancer.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction.

In one aspect of the invention, a method for the treatment of cancer (e.g. breast cancer) is provided. In some embodiments, the treatment of cancer comprises administering a therapeutically effective amount of the prodrug of the present invention to a subject in need thereof, in such amounts and for such time as is necessary to achieve the desired result. In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

In one aspect of the invention, a method for administering inventive compositions to a subject suffering from cancer (e.g. breast cancer) is provided. In some embodiments, administering the prodrug to a subject in such amounts and for such time as is necessary to achieve the desired result (i.e. treatment of cancer). In certain embodiments of the present invention a "therapeutically effective amount" of the prodrug is that amount effective for treating, alleviating, ameliorating, relieving, delaying onset of, inhibiting progression of, reducing severity of, and/or reducing incidence of one or more symptoms or features of cancer.

EXAMPLES

Example 1

Figure 1:
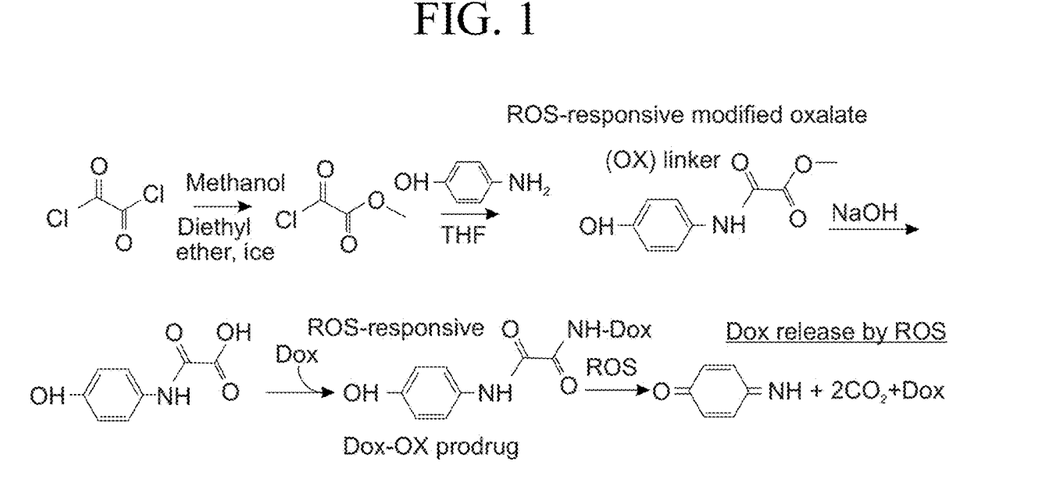
FIG. 1 depicts an exemplary synthetic scheme and release routes of the Dox-OX prodrug according to an embodiment of the present application.

We synthesized a ROS-responsive oxylate-Dox (Dox-OX) prodrug that can be triggered by intracellular ROS within tumor tissues and by proton radiation (FIG. 1). First, methanol was added dropwise to a solution of oxalyl chloride mixed in diethyl ether chilled at 0° C., at a molar ratio of 1 to 1 and stirred for at least 2 hours. Without further purification, diethyl ether was removed using a rotary evaporator. Then this product was added dropwise to a solution of 4-aminophenol partially dissolved in THF, to form our novel ROS-responsive oxalate linker. Then, the methoxy group was removed using sodium hydroxide (NaOH), neutralized by concentrated HCl, and extracted using ethyl acetate. In the last step, doxorubicin was reacted with the linker using HATU coupling in the presence of TEA. For this reaction, the acid group of the linker was activated using the HATU reagent. Doxorubicin with excess TEA was added to this solution to form the Dox-OX prodrug. The synthesis of the Dox-OX prodrug was validated using mass spectrometry (MS) and $^1$H NMR (data not shown).

The Dox-OX prodrug was subjected to ROS using $H_2O_2$ to determine the release rate of Dox from the prodrug analyzed by HPLC. Intracellular ROS level in cancerous cells was reported to reach up to ~100 µM $H_2O_2$. Thus, phosphate buffered saline ("PBS") with 50 µM $H_2O_2$ (i.e. a half of the maximum level reported) was used to simulate the intracellular ROS level in cancer cells without irradiation. The Dox-OX prodrug showed very stable Dox release profiles in PBS at pH 7.4 and 10 and 50%.

Figure 3A:
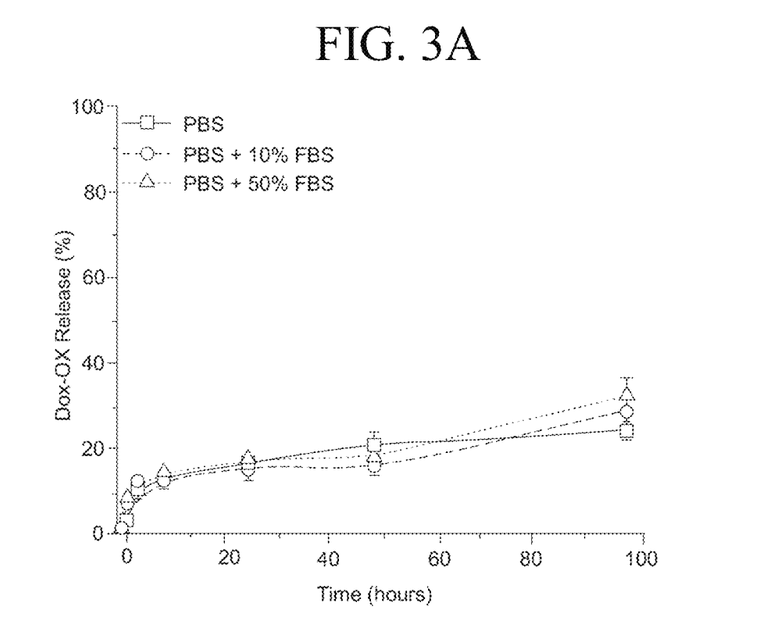
FIG. 3A is a graph showing Dox release kinetics of the Dox-OX prodrug in PBS, PBS with 10% and 50% FBS at pH 7.4.
Figure 3B:
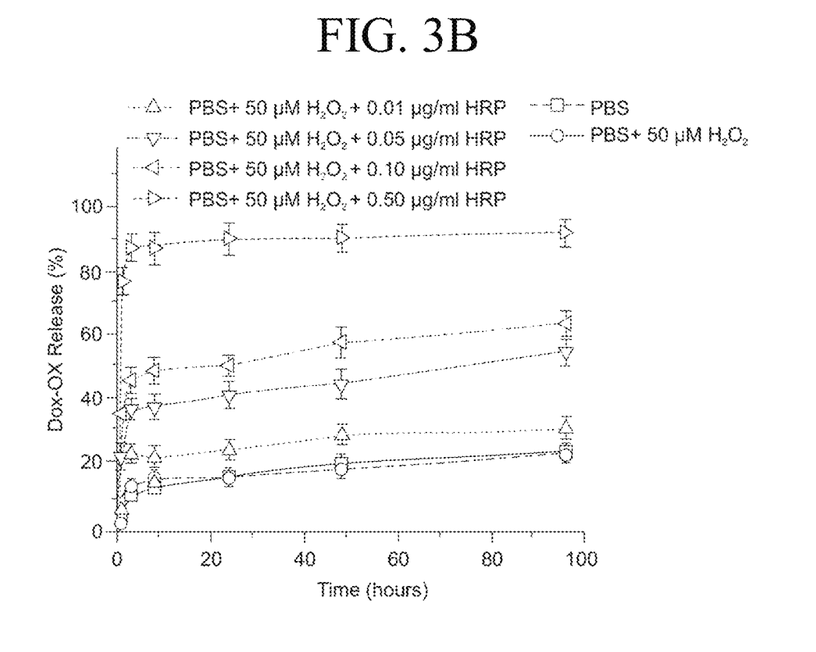
FIG. 3B is a graph showing Dox release kinetics of the Dox-OX prodrug in 50 μM $H_2O_2$ and different HRP concentrations.

Fetal bovine serum ("FBS") in PBS, showed only <~30% of Dox release within 96 hrs (FIG. 3A). The FBS solution was used to evaluate potential premature drug leakage during systemic circulation, and 50% FBS in PBS is high enough to simulate the condition. While adding 50 µM of $H_2O_2$ to PBS did not trigger the Dox release, adding different concentrations of horseradish peroxidase (HRP) to the solution of 50 µM $H_2O_2$ in PBS, released Dox from the Dox-OX prodrug (FIG. 3B). It should be noted that most of Dox was released within a few hours, showing very favorable fast release kinetics. HRP is an enzyme catalyzing the oxidation by $H_2O_2$, simulates the production of intracellular ROS with OH radicals, and speeds up the Dox release. These release results demonstrate that the Dox-OX prodrug has great potential for suppressing premature Dox leakage during systemic circulation and releasing Dox at tumor sites for maximum therapeutic efficacy.

Figure 4A:
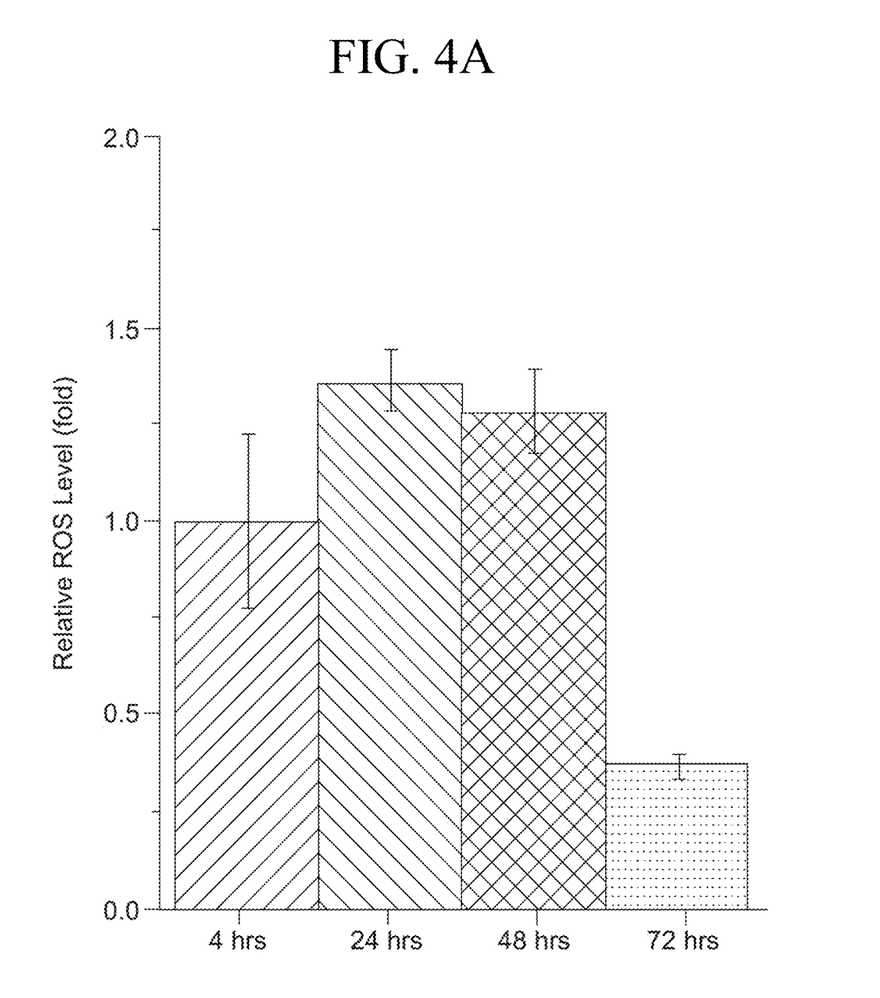
FIG. 4A is a graph of in vitro test results of an MTS assay using the MDA-MB-231 cell line showing ROS level generated as a function of time.
Figure 4B:
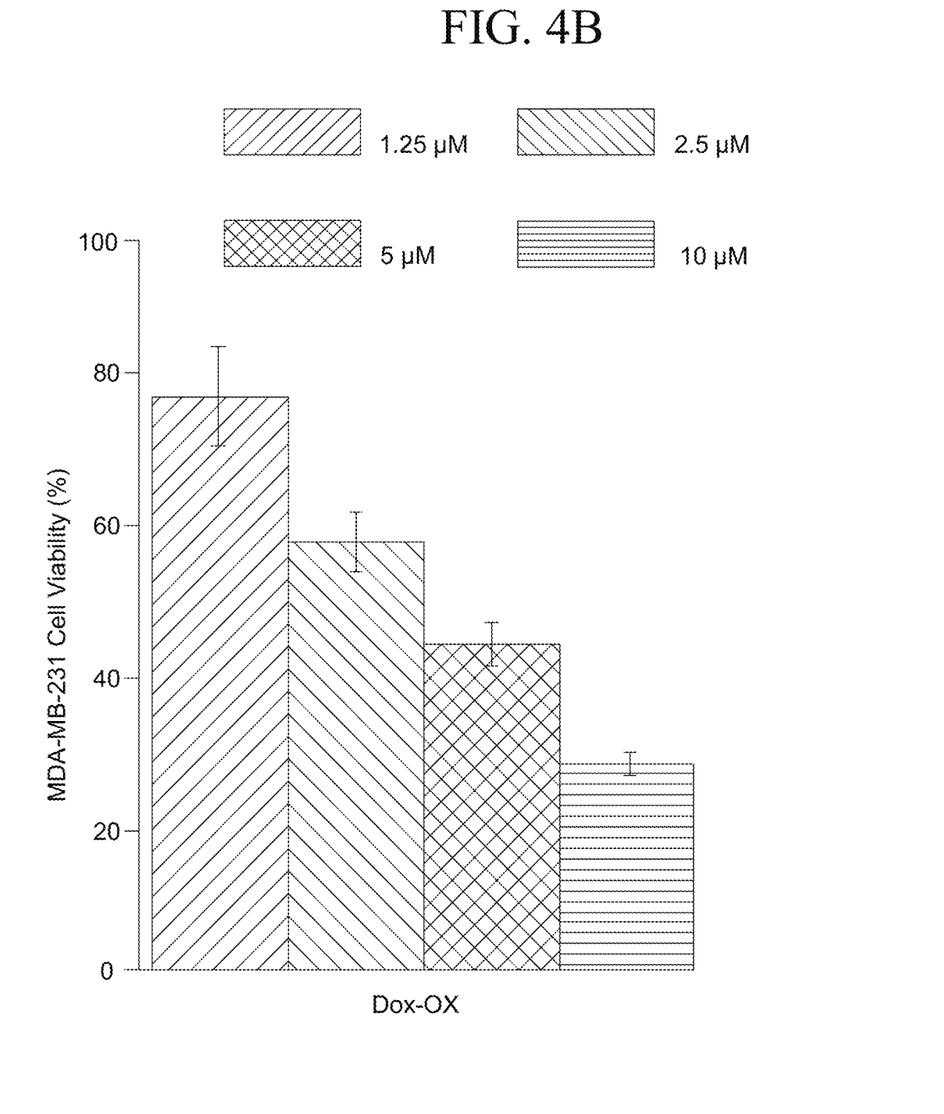
FIG. 4B is a graph of in vitro test results of an MTS assay using the MDA-MB-231 cell line showing cell viability for Dox-OX prodrug after 48-hr incubation.

Intracellular ROS level in the MBC MDA-MB-231 cell line was measured in vitro using 2', 7'-dichlorofluorescin diacetate (DCF) fluorescent probe (FIG. 4A). The intracellular ROS level was kept at almost a constant level up to 48 hrs and decreased after 72 hrs. In vitro test cannot usually be run longer than ~48 hrs. However, the cell viability of the MDA-MB-231 cells clearly responded to the Dox-OX prodrug at different concentrations after 48-hr incubation without irradiation (FIG. 4B). These in vitro results for the intracellular ROS level and cell viability without irradiation along with the release result show that the Dox-OX prodrug of the present invention may provide sustained release during systemic circulation and controlled release at the tumor site.

CONCLUSION

The present invention allows the use of FDA-approved, very potent and common therapeutics such as Dox and cisplatin to treat various cancers including breast, bladder, lymphoma, leukemia, lung, head and neck, brain, cervical, ovarian, and many others in a safer, more targeted approach. The present prodrugs are responsive to radiation, which will lead to safe and effective chemoradiation therapy for the quality treatments of cancer patients.

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A compound of the formula:

or a pharmaceutically acceptable salt or solvate thereof, wherein, independently for each occurrence:

X is NH or O;
Y is O, S, or $NR^2$;
Z is OH, $OR^2$, $NHR^2$, or $SR^2$;
$R^1$ is a chemotherapeutic agent selected from the group consisting of alkylating agents;
purine and pyrimidine analogs and derivatives; topoisomerase inhibitors; taxanes;
antifolates; angiogenesis inhibitors; anti-tumor monoclonal antibodies; cytotoxic antibiotics; anthracycline antibiotics; triterpenoid Stat3 inhibitors; and physiologically acceptable salts thereof; and
$R^2$ is a polymer selected from the group consisting of poly-L-lactic acid-polyethylene glycol (PLLA-PEG), poly-D,L-lactic acid-polyethylene glycol (PDLLA-PEG), poly(lactide-co-glycolide)-polyethylene glycol (PLGA-PEG), Poly (L-aspartic acid), Poly (L-lysine), Poly (L-glutamic acid), Poly (L-arginine), and Poly (L-ornithine); or $R^2$ is a linkage to said polymer.

2. The compound of claim 1 wherein the compound is encapsulated in a nanoparticle.

3. The compound of claim 2 wherein the compound is physically encapsulated in a nanoparticle.

4. The compound of claim 3 wherein the compound is hydrophobic and the nanoparticle comprises a polymer selected from the group consisting of PLLA-PEG, PDLLA-PEG and PLGA-PEG.

5. The compound of claim 3 wherein the compound is hydrophilic and the nanoparticle comprises a polymer selected from the group consisting of albumin, Poly (L-aspartic acid), Poly (L-lysine), Poly (L-glutamic acid), Poly (L-arginine), and Poly (L-ornithine).

6. The compound of claim 1 wherein $R^1$ is an anthracycline antibiotic selected from the group consisting of doxorubicin, epirubicin, daunorubicin, valrubicin and idarubicin.

7. The compound of claim 1 wherein $R^1$ is doxorubicin.

8. The compound of claim 1 wherein $R^1$ is an alkylating agent selected from the group consisting of cisplatin, carboplatin, oxaliplatin, mechlorethamine, cyclophosphamide, chlorambucil and ifosfamide.

9. The compound of claim 1 wherein $R^1$ is cisplatin.

10. The compound of claim 1 wherein X is NH.

11. The compound of claim 1 wherein Y is O.

12. The compound of claim 1 wherein Z is $OR^2$.

13. A method for treatment of cancer in a subject in need thereof, the method comprising: administering to the subject a therapeutically effective amount of a compound having the formula:

or a pharmaceutically acceptable salt or solvate thereof, wherein, independently for each occurrence:

X is NH or O;

Y is O, S, or $NR^2$;

Z is OH, $OR^2$, $NHR^2$, or $SR^2$;

$R^1$ is a chemotherapeutic agent selected from the group consisting of alkylating agents; purine and pyrimidine analogs and derivatives; topoisomerase inhibitors; taxanes; antifolates; angiogenesis inhibitors; anti-tumor monoclonal antibodies; cytotoxic antibiotics; anthracycline antibiotics; triterpenoid Stat3 inhibitors; and physiologically acceptable salts thereof; and $R^2$ is a polymer selected from the group consisting of PLLA-PEG, PDLLA-PEG, PLGA-PEG, Poly (L-aspartic acid), Poly (L-lysine), Poly (L-glutamic acid), Poly (L-arginine), and Poly (L-ornithine); or $R^2$ is a linkage to said polymer.

14. The method of claim 13 wherein the compound is encapsulated in a nanoparticle.

15. The method of claim 14 wherein the compound is physically encapsulated in a nanoparticle.

16. The method of claim 15 wherein the compound is hydrophobic and the nanoparticle comprises a polymer selected from the group consisting of PLLA-PEG, PDLLA-PEG and PLGA-PEG.

17. The method of claim 15 wherein the compound is hydrophilic and the nanoparticle comprises a polymer selected from the group consisting of albumin, Poly (L-aspartic acid), Poly (L-lysine), Poly (L-glutamic acid), Poly (L-arginine), and Poly (L-ornithine).

18. The method of claim 13 wherein $R^1$ is an anthracycline antibiotic selected from the group consisting of doxorubicin, epirubicin, daunorubicin, valrubicin and idarubicin.

19. The method of claim 13 wherein $R^1$ is doxorubicin.

20. The method of claim 13 wherein X is NH, Y is O and Z is $OR^2$.

21. The method of claim 13 further comprising administering radiation to the subject in conjunction with the compound.

22. The method of claim 21 wherein the radiation is proton or photon radiation.

* * * * *